United States Patent
Hagiya

(10) Patent No.: US 7,638,655 B2
(45) Date of Patent: Dec. 29, 2009

(54) METHOD FOR PRODUCTING 4-(METHYLTHIO)BUTANE-1,2-DIOL

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 131 days.

(21) Appl. No.: 11/991,734

(22) PCT Filed: Aug. 11, 2006

(86) PCT No.: PCT/JP2006/316195

§ 371 (c)(1),
(2), (4) Date: Mar. 10, 2008

(87) PCT Pub. No.: WO2007/032177

PCT Pub. Date: Mar. 22, 2007

(65) Prior Publication Data

US 2009/0259075 A1   Oct. 15, 2009

(30) Foreign Application Priority Data

Sep. 12, 2005 (JP) ............................. 2005-263463

(51) Int. Cl.
*C07C 319/04* (2006.01)

(52) U.S. Cl. .......................................... 568/46; 568/62
(58) Field of Classification Search ................... 568/46, 568/62
See application file for complete search history.

(56) References Cited

U.S. PATENT DOCUMENTS 7,485,757 B2 *   2/2009  Hagiya ..................... 568/46
2004/0063650 A1  4/2004  Shiozaki et al.

FOREIGN PATENT DOCUMENTS

EP   1 260 500 A1   11/2002
JP   2002-121182    4/2002

OTHER PUBLICATIONS

Steadman, Thomas R. et al., "A Methionine Substitute: 4-Methylthiobutane-1,2-diol", J. Agric. Food Chem., vol. 23, No. 6, 1975, pp. 1137-1144.

* cited by examiner

*Primary Examiner*—Sikarl A Witherspoon
(74) *Attorney, Agent, or Firm*—Foley & Lardner LLP

(57) ABSTRACT

A method for producing 4-(methylthio)butane-1,2-diol which comprises reacting 3-butene-1,2-diol with methanethiol in the presence of at least one nitrogen-containing compound selected from a nitrogen-containing aromatic compound and a tertiary amine compound and a carboxylic acid compound.

9 Claims, No Drawings

METHOD FOR PRODUCING 4-(METHYLTHIO)BUTANE-1,2-DIOL

TECHNICAL FIELD

The present invention relates to a method for producing 4-(methylthio)butane-1,2-diol.

BACKGROUND ART 4-(Methylthio)butane-1,2-diol is an important compound as an intermediate of pharmaceuticals and a methionine analog (e.g. EP 338735 B and J. Agric. Food Chem., 23, 1137 (1975)). As the method for producing 4-(methylthio)butane-1,2-diol, a method comprising reacting 3-butene-1,2-diol with methanethiol in the presence of tert-butyl perphthalate and a method comprising reacting 3-butene-1,2-diol with methanethiol in the presence of a boron compound are described in J. Agric. Food Chem., 23, 1137 (1975) and EP 1260500 A, respectively.

DISCLOSURE OF THE INVENTION

The present invention provides a method for producing 4-(methylthio)butane-1,2-diol which comprises reacting 3-butene-1,2-diol with methanethiol in the presence of at least one nitrogen-containing compound selected from a nitrogen-containing aromatic compound and a tertiary amine compound and a carboxylic acid compound.

BEST MODE FOR CARRYING OUT THE PRESENT INVENTION

As 3-butene-1,2-diol, commercially available one may be used and for example, one produced according to known methods such as a method comprising reacting 1,2-epoxy-3-butene with water in the presence of sulfuric acid catalyst (e.g. U.S. Pat. No. 5,250,743) and a method comprising isomerizing 2-butene-1,4-diol in the presence of dirhenium heptoxide (e.g. U.S. Pat. No. 5,336,815) may be used.

As methanethiol, commercially available one may be used and one produced from methanol and hydrogen sulfide. Gaseous methanethiol may be used and liquid methanethiol may be used. Liquid methanethiol can be prepared, for example, by a method comprising bringing gaseous methanethiol into a container cooled below the boiling point thereof (6° C.) to condense it.

The amount of methanethiol to be used is usually 1 mole or more relative to 1 mole of 3-butene-1,2-diol. There is no upper limit particularly and considering economical viewpoint, the amount thereof is practically 10 moles or less relative to 1 mole of 3-butene-1,2-diol.

In the present invention, at least one nitrogen-containing compound selected from a nitrogen-containing aromatic compound and a tertiary amine compound (hereinafter, simply referred to as the nitrogen-containing compound) is used, and the nitrogen-containing aromatic compound is preferably used.

Examples of the nitrogen-containing aromatic compound include a monocyclic or condensed-ring type nitrogen-containing aromatic compound wherein at least one among atoms composed of the aromatic ring is a nitrogen atom. The nitrogen-containing aromatic compound may be substituted with at least one substituent. Examples of the substituent include a halogen atom such as a fluorine, chlorine and bromine atom; a C1-C4 alkyl group such as a methyl, ethyl, n-propyl, isopropyl, n-butyl, isobutyl, sec-butyl and tert-butyl group; a C1-C4 alkoxy group such as a methoxy, ethoxy, n-propoxy, isopropoxy, n-butoxy, isobutoxy, sec-butoxy and tert-butoxy group; a C2-C5 alkoxycarbonyl group such as a methoxycarbonyl, ethoxycarbonyl, n-propoxycarbonyl, iso-propoxycarbonyl, n-butoxycarbonyl and tert-butoxycarbonyl group; a C2-C8 dialkylamino group such as a dimethylamino and diethylamino group; and a carbamoyl group.

Examples of the nitrogen-containing aromatic compound include pyridine, piperidine, pyrazine, imidazole, benzimdazole, phenanethroline, oxazole, thiazole, quinoline, isoquinoline, 2-methylpyridine, 3-methylpyridine, 4-methylpyridine, 2-chloropyridine, 3-chloropyridine, 4-chlorpyridine, 2,3,5-collidine, 2,4,6-collidine, nicotinamide, methyl nicotinate, N-methylimidazole and 2-chloroquinoline. Among them, a pyridine compound which may be substituted with at least one substituent selected from the halogen atom, the C1-C4 alkyl group, the C1-C4 alkoxy group, the C2-C5 alkoxycarbonyl group, the C2-C8 dialkylamino group and the carbamoyl group such as pyridine, 2-methylpyridine, 3-methylpyridine, 4-methylpyridine, 2-chloropyridine, 3-chloropyridine, 4-chlorpyridine, 2,3,5-collidine, 2,4,6-collidine, nicotinamide and methyl nicotinate is preferable. As the nitrogen-containing aromatic compound, a commercially available one is usually used.

Examples of the tertiary amine compound include a C3-C20 tertiary amine compound such as trimethylamine, triethylamine, tri(n-propyl)amine, tri(n-butyl)amine, tri(n-pentyl)amine, tri(n-hexyl)amine, dimethyl(n-octyl)amine, dimethyl(n-decyl)amine, dimethyl(n-dodecyl)amine, dimethyl(n-tetradecyl)amine, dimethyl(n-hexadecyl)amine, dimethyl(n-octadecyl)amine, di(n-hexyl)methylamine, di(n-octyl)methylamine, dimethylbenzylamine, di(n-butyl)benzylamine, N,N-dimethylaniline, N,N-di(n-butyl)aniline, N,N-di(n-hexyl)aniline, N-methylmorpholine, N-(n-butyl) morpholine, N-(n-octyl)morpholine, N-(n-decyl)morpholine, N-(n-dodecyl)morpholine, N-methylpyrrolidine, N-(n-butyl)pyrrolidine, N-(n-hexyl)pyrrolidine, N-(n-octyl) pyrrolidine, N-(n-decyl)pyrrolidine, N-(n-dodecyl) pyrrolidine, N-methylpiperidine, N-(n-butyl)piperidine, N-(n-hexyl)piperidine, N-(n-octyl)piperidine, N-(n-decyl) piperidine and N-(n-dodecyl)piperidine.

As the tertiary amine compound, a commercially available one is usually used.

The amount of the nitrogen-containing compound to be used is usually 0.001 mole or more relative to 1 mole of 3-butene-1,2-diol, and there is no specific upper limit and it is practically 1 mole or less relative to 1 mole of 3-butene-1,2-diol considering economical viewpoint.

Examples of the carboxylic acid compound include a C1-C20 aliphatic carboxylic acid compound and C7-C20 aromatic carboxylic acid compound, and the C1-C20 aliphatic carboxylic acid compound is preferable.

Examples of the C1-C20 aliphatic carboxylic acid compound include formic acid, acetic acid, propionic acid, butanoic acid, pentanoic acid, hexanoic acid, oxalic acid, lactic acid, succinic acid, adipic acid, maleic acid and fumaric acid. Examples of the C7-C20 aromatic carboxylic acid compound include benzoic acid, salicylic acid, acetylsalicylic acid and terephthalic acid.

As the carboxylic acid compound, a commercially available one is usually used.

The amount of the carboxylic acid compound to be used is usually 0.3 to 10 moles and preferably 1 to 5 moles relative to 1 mole of the nitrogen-containing compound.

The reaction temperature is usually −10 to 100° C. and preferably 0 to 50° C. The reaction time is usually 0.5 to 24 hours.

The reaction is usually conducted under an ordinary pressure or pressurized condition. The reaction may be conducted under reduced pressure condition.

The reaction of 3-butene-1,2-diol and methanethiol is usually carried out in the absence of a solvent, and it may be conducted in the presence of the solvent. The solvent is not particularly limited in so far as it does not prevent the reaction. Examples thereof include water; a hydrocarbon solvent such as hexane, heptane and toluene; a halogenated hydrocarbon solvent such as chlorobenzene and chloroform; an ether solvent such as diethyl ether, methyl tert-butyl ether and tetrahydrofuran; an ester solvent such as ethyl acetate; a tertiary alcohol solvent such as tert-butanol; and a nitrile solvent such as acetonitrile and propionitrile. They may be used alone or in a form of a mixture. The amount thereof to be used is not particularly limited, and it is practically 100 parts by weight or less per 1 part by weight of 3-butene-1,2-diol in the viewpoint of volume efficacy.

The reaction of 3-butene-1,2-diol and methanethiol is usually conducted by mixing the nitrogen-containing compound, the carboxylic acid compound, 3-butene-1,2-diol and methanethiol, if necessary, in the presence of the solvent, and the mixing order is not particularly limited. The nitrogen-containing compound and the carboxylic acid compound may be previously mixed.

When the reaction is conducted under an ordinary pressure condition, the reaction is usually conducted by a method comprising adjusting a mixture obtained by mixing the nitrogen-containing compound, the carboxylic acid compound, 3-butene-1,2-diol, methanethiol, and if necessary, the solvent, at a given temperature and blowing gaseous methanethiol into them.

When the reaction is conducted under a pressurized condition, the reaction is conducted, for example, by a method comprising adding the nitrogen-containing compound, the carboxylic acid compound, 3-butene-1,2-diol, and if necessary, the solvent into a container capable of sealing such as autoclave, sealing the container and pressing gaseous methanethiol into it at a given temperature, and a method comprising adding the nitrogen-containing compound, the carboxylic acid compound, 3-butene-1,2-diol, liquid methanethiol, and if necessary, the solvent into the above-mentioned sealing container, sealing the container and adjusting at a given temperature. In the case of adjusting a mixture obtained by mixing 3-butene-1,2-diol, methanethiol, the nitrogen-containing compound, the carboxylic acid compound, and if necessary, the solvent at a given temperature to effect reaction or in the case of mixing 3-butene-1,2-diol with methanethiol followed by adding the nitrogen-containing compound and the carboxylic acid compound thereto to effect reaction, the amount of methanethiol in the mixture containing 3-butene-1,2-diol and methanethiol is preferably 4 moles or less relative 1 mole of 3-butene-1,2-diol in order to start the reaction smoothly.

The progress of the reaction can be confirmed by a conventional analytical means such as gas chromatography, high performance liquid chromatography, thin layer chromatography, nuclear magnetic resonance spectrum analysis and infrared adsorption spectrum analysis.

After completion of the reaction, an organic layer containing 4-(methylthio)butane-1,2-diol can be obtained by removing methanethiol remained from the reaction mixture, and then, if necessary, adding water or a water-insoluble organic solvent thereto, followed by extracting. 4-(methylthio)butane-1,2-diol can be isolated by concentrating the organic layer obtained. The organic layer obtained may be concentrated after washing with water, an aqueous acid solution or an aqueous alkali solution.

Examples of the method for removing methanethiol remained from the reaction mixture include a method comprising concentrating the reaction mixture and a method comprising blowing an inert gas such as nitrogen gas into the reaction mixture.

Examples of the water-insoluble organic solvent include an ester solvent such as ethyl acetate; an ether solvent such as methyl tert-butyl ether; and a halogenated hydrocarbon solvent such as chloroform, dichloromethane and dichloroethane. The amount thereof to be used is not particularly limited.

As the aqueous acid solution, an aqueous mineral acid solution is usually used and the concentration thereof and the amount thereof to be used are not particularly limited. As the aqueous alkali solution, an aqueous solution of a metal hydroxide such as sodium hydroxide and potassium hydroxide; a metal carbonate such as sodium carbonate and potassium carbonate; and an alkali metal hydrogen carbonate such as sodium hydrogen carbonate and potassium hydrogen carbonate is usually used and the concentration thereof and the amount thereof to be used are not particularly limited.

4-(methylthio)butane-1,2-diol obtained may be further purified by a conventional purification means such as distillation and column chromatography.

EXAMPLES

The present invention will be further illustrated by Examples in detail below, but the present invention is not limited by these Examples.

Example 1

To a 50 ml autoclave equipped with a magnetic stirrer, 2000 mg of 3-butene-1,2-diol, 9 mg of pyridine and 14 mg of acetic acid were added. After cooling the mixture obtained at an inner temperature of 0° C., 1500 mg of liquid methanethiol was added thereto. The autoclave was sealed, and then the mixture was stirred at 40° C. for 4 hours to effect reaction. The pressure (gauge pressure) of internal autoclave at the point of starting the reaction was 2.5 kg/cm$^2$ (corresponding to 0.25 MPa) and the pressure (gauge pressure) of internal autoclave at the point of completion of the reaction was 0.5 kg/cm$^2$ (corresponding to 0.05 MPa). After completion of the reaction, the pressure was released to the ordinary pressure and methanethiol remained was removed by blowing nitrogen into the reaction mixture, and 10 g of ethyl acetate was added thereto. The solution obtained was analyzed by gas chromatography internal standard method to find the yield of 4-(methylthio)butane-1,2-diol was 94% and 3-butene-1,2-diol was remained in 5%.

Example 2

According to a similar manner as that of Example 1, 4-(methylthio)butane-1,2-diol was obtained except that 28 mg of 2,4,6-collidine was used in place of 9 mg of pyridine and 26 mg of 80% formic acid was used in place of 14 mg of acetic acid. The yield was 95% and 3-butene-1,2-diol was remained in 4%.

Example 3

According to a similar manner as that of Example 1, 4-(methylthio)butane-1,2-diol was obtained except that 29 mg of quinoline was used in place of 9 mg of pyridine and 34 mg of propionic acid was used in place of 14 mg of acetic acid. The yield was 58% and 3-butene-1,2-diol was remained in 40%.

Example 4

According to a similar manner as that of Example 1, 4-(methylthio)butane-1,2-diol was obtained except that the amount of pyridine to be used was 18 mg and 55 mg of benzoic acid was used in place of 14 mg of acetic acid. The yield was 39% and 3-butene-1,2-diol was remained in 58%.

Example 5

According to a similar manner as that of Example 1, 4-(methylthio)butane-1,2-diol was obtained except that 22 mg of triethylamine was used in place of 9 mg of pyridine and the amount of acetic acid was 30 mg. The yield was 40% and 3-butene-1,2-diol was remained in 58%.

INDUSTRIAL APPLICABILITY

According to the present invention, 4-(methylthio)butane-1,2-diol, which is an important as an intermediate of pharmaceuticals and a methionine analog, can be produced under a mild condition and it is industrially advantageous.

The invention claimed is:

1. A method for producing 4-(methylthio)butane-1,2-diol which comprises reacting 3-butene-1,2-diol with methanethiol in the presence of at least one nitrogen-containing compound selected from a nitrogen-containing aromatic compound and a tertiary amine compound and a carboxylic acid compound.

2. The method according to claim 1, wherein the nitrogen-containing aromatic compound is a monocyclic or condensed-ring nitrogen-containing aromatic compound wherein the number of carbon atoms composed of the aromatic ring is 3 to 20, and at least one is a nitrogen atom among the atoms composed of the aromatic ring, and which may be substituted with at least one substituent selected from a halogen atom, a C1-C4 alkyl group, a C1-C4 alkoxy group, a C2-C5 alkoxycarbonyl group, a C2-C10 dialkylamino group and a carbamoyl group.

3. The method according to claim 1, wherein the nitrogen-containing aromatic compound is a pyridine compound which may be substituted with at least one substituent selected from a halogen atom, a C1-C4 alkyl group, a C1-C4 alkoxy group, a C2-C5 alkoxycarbonyl group, a C2-C8 dialkylamino group and a carbamoyl group.

4. The method according to claim 3, wherein the pyridine compound which may be substituted with at least one substituent selected from a halogen atom, a C1-C4 alkyl group, a C1-C4 alkoxy group, a C2-C5 alkoxycarbonyl group, a C2-C8 dialkylamino group and a carbamoyl group is pyridine, 2-methylpyridine, 3-methylpyridine, 4-methylpyridine, 2-chloropyridine, 3-chloropyridine, 4-chloropyridine, 2,3,5-collidine, 2,4,6-collidine, nicotinamide or methyl nicotinate.

5. The method according to claim 1, wherein the tertiary amine compound is a C3-C20 tertiary amine compound.

6. The method according to claim 1, wherein the carboxylic acid compound is a C1-C20 aliphatic carboxylic acid compound or a C7-C20 aromatic carboxylic acid compound.

7. The method according to claim 6, wherein the C1-C20 aliphatic carboxylic acid compound is formic acid, acetic acid, propionic acid, butanoic acid, pentanoic acid, hexanoic acid, oxalic acid, lactic acid, succinic acid, adipic acid, maleic acid or fumaric acid.

8. The method according to claim 6, wherein the C7-C20 aromatic carboxylic acid compound is benzoic acid, salicylic acid, acetylsalicylic acid or terephthalic acid.

9. The method according to claim 1, wherein the amount of the carboxylic acid to be used is 0.3 to 10 moles relative to 1 mole of at least one nitrogen-containing compound selected from a nitrogen-containing aromatic compound and a tertiary amine compound and a carboxylic acid compound.

* * * * *